United States Patent [19]
Corrales

[11] 3,941,119
[45] Mar. 2, 1976

[54] MEANS FOR INTRODUCING AND GUIDING OBJECTS INTO BODY CAVITIES AND BLOOD VESSELS

[76] Inventor: Mario Corrales, Artillergatan 45, Stockholm, Sweden

[22] Filed: July 19, 1974

[21] Appl. No.: 489,928

[30] Foreign Application Priority Data
July 20, 1973 Sweden.............................. 7310149

[52] U.S. Cl............. 128/2 M; 128/DIG. 9; 128/343; 128/348
[51] Int. Cl.²........................................ A61M 25/00
[58] Field of Search . 128/2 R, 2 M, 2.05 R, DIG. 9, 128/348, 349 R, 350 R, 341, 343

[56] References Cited
UNITED STATES PATENTS

| | | | |
|---|---|---|---|
| 3,570,485 | 3/1971 | Reilly................................... | 128/348 |
| 3,687,142 | 8/1972 | Leibinzohn.......................... | 128/348 |
| 3,749,085 | 7/1973 | Willson et al. ...................... | 128/2 B |
| 3,794,041 | 2/1974 | Frei et al............................. | 128/2 M |
| 3,844,274 | 10/1974 | Nordstrom......................... | 128/2 M |

OTHER PUBLICATIONS
USCI Catalogue 1964 p. 32.

*Primary Examiner*—Dalton L. Truluck
*Attorney, Agent, or Firm*—Hill, Gross, Simpson, Van Santen, Steadman, Chiara & Simpson

[57] ABSTRACT

Means for introducing and guiding objects such as liquids or instruments in cavities or blood vessels in the body of a patient, comprising a cannula for insertion in the body at the place where the object is to be introduced into the body, a gold chain for insertion into the cannula and penetration into the body under the effect of gravity, and a soft, flexible catheter of a dimension for passing through the cannula and over the flexible member when inserted and for permitting the flexible member to be drawn out after insertion of the catheter.

10 Claims, 1 Drawing Figure

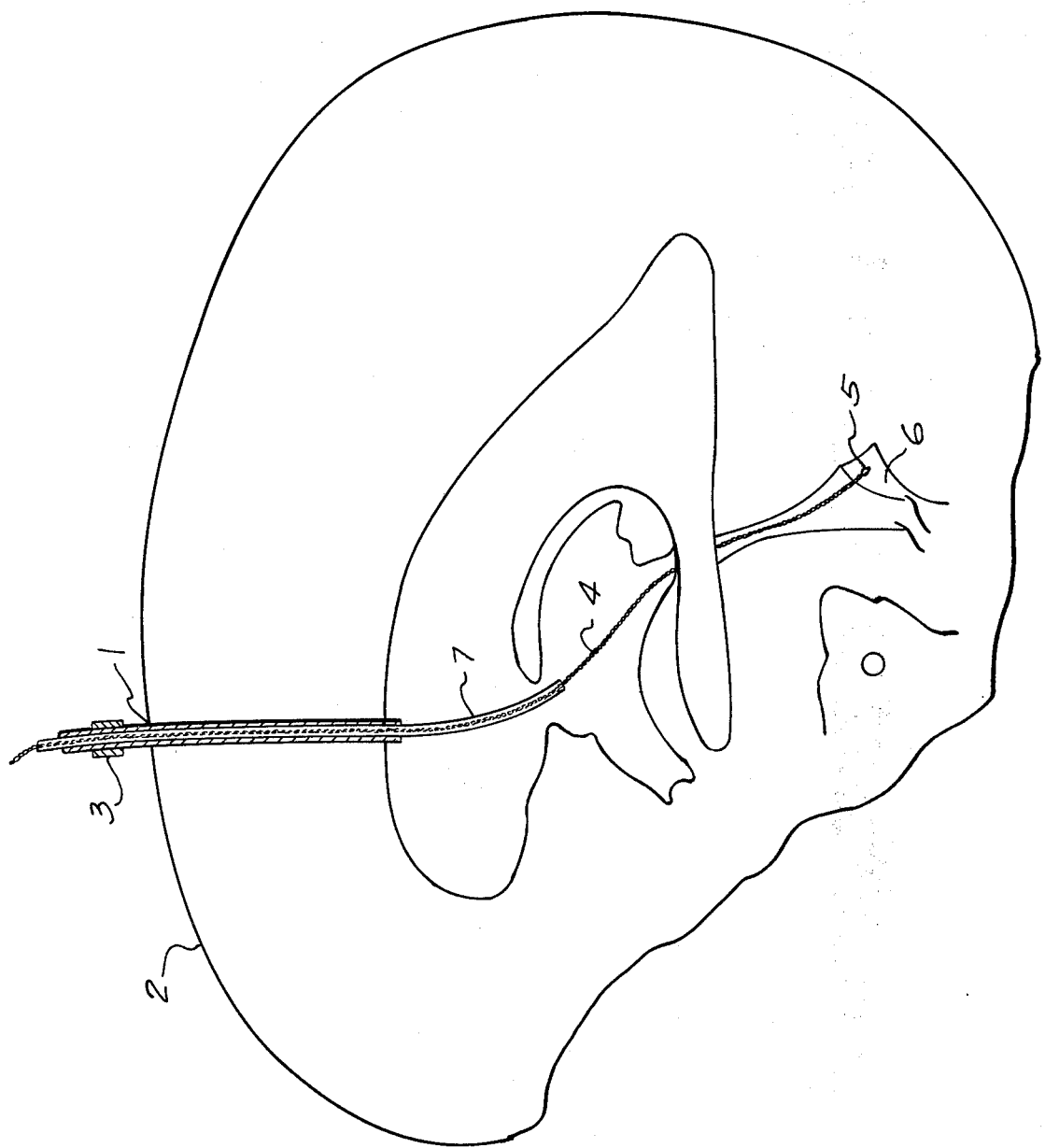

3,941,119

MEANS FOR INTRODUCING AND GUIDING OBJECTS INTO BODY CAVITIES AND BLOOD VESSELS

BACKGROUND OF THE INVENTION

1. Field of the Invention

This invention relates to means for introducing and guiding objects in cavities or blood vessels in the body of a patient.

2. Prior Art

Many methods have been proposed in the past, for inserting catheters into the body of a patient. In this connection, there have been used, for example, previously primarily bent catheters made of a relatively rigid material, which can be straightened or bent at the point thereof with the aid of inserted guide means. Catheters have also been guided by magnetically influencing the direction in which their point is inserted. In connection with cerebral examinations, it is known to insert an object straight through the brain tissue and through the ventricles. This often results in damage, however.

Common to all methods known to me is that they do not fulfil all requirements associated with selective ventriculography and the study of the vascular system, for which much more conformable and guidable auxiliary devices are required.

SUMMARY OF THE INVENTION

The invention provides means for introducing and guiding objects in cavities or blood vessels in the body of a patient, a cannula for insertion in the body at the place where the object is to be introduced into the body, receives a flexible elongated member and penetration into the body beyond the cannula under the effect of gravity, and a soft, flexible catheter dimensioned for passing radially therebetween to enable the flexible member to be drawn out thereafter.

In use of the means according to the invention, the patient, or that portion of the body thereof to be examined, is arranged so as to be movable in all directions. A cannula is inserted at the place where the object is to be inserted into the body. A flexible chain is introduced into the cannula and one end of the chain is fed into the body gravitationally, by changing the position of the patient or of the examined portion of the body thereof, preferably while visibilizing the desired guide direction. Thereafter a soft, flexible catheter is passed over the infed chain to the desired length and the chain is withdrawn, out of the catheter.

To facilitate the introduction of the chain into the body, the insertion end of the chain may be provided with a soft, rounded weight, for example in the shape of an olive, having generally the same thickness as the chain but a not too great longitudinal extension. A thin filament of rigid material may be attached to the outer end of the chain, for the purpose of guiding the catheter as it is fitted over the chain. The insertion of the chain can be facilitated, by supplementing the movement of the chain in the body due to gravity, with magnetic forces, in which case the chain comprises wholly or partially magnetic material. It is also possible to use an extremely flexible chain of known type, which can be locked in an adopted straight or curved position by means capable of being actuated from without. An example of such a chain is one comprising links which abut each other, either directly or indirectly, via spherical slide surfaces and which are arranged on a central center string which, when tensioned with an axial force relative to the row of links, creates an increase in the friction between the links and a "locking" of the chain in the position adopted thereby. At one or more positions along its length, and at least at its insertion end, the chain may be provided with radio-opaque points, to facilitate control of the insertion of the catheter.

By the use of a chain to guide a highly flexible object, such as a catheter, for insertion into the body, by gravitationally falling into body cavities, an advantage is gained in which even sharp bends can be followed, without structures or walls being damaged. In the foregoing, flexible member object has been referred to as a "chain." Other objects which are extremely flexible and which have sufficient weight and mechanical strength may be used, for example a catheter which, in accordance with the above, has been provided with a weight at the insertion end. Such object, or a part thereof, should be made of a material having a high specific gravity, however, such as gold.

IN THE DRAWING

The drawing shows examination of the fourth ventricle of the brain.

AS SHOWN ON THE DRAWINGS:

A cannula 3 is inserted in a hole 1 suitably located in a calvarium 2. By placing the patient in a universal inclinable and rotatable chair or the like, the skull can be made to assume different positions. The direction of the cannula is selected in accordance with that part of the brain to be examined, in the illustrated case, approximately in the center line of the brain towards the outer auditory duct. The direction of the cannula can be controlled by means of X-ray, preferably by means of X-ray television. An extremely flexible chain 4 is then inserted in the cannula and falls gravitationally against a lateral ventricle. The position of the end of the chain, which may be provided with an olive-shaped weight 5, is checked by means of X-ray television. Insertion of the chain is controlled by small movements of the patient's head, and by changing the position of the chair. In order to pass the chain through the foramen of Monro, the head is tilted slightly to one side, whereafter it is moved forwards and backwards. In order that the fourth ventricle 6 beneath the lesser brain can be reached, there is threaded onto the chain an extremely flexible catheter 7 provided at least at the insertion end with a radio-opaque point to facilitate control i.e. identification of location, by television apparatus, so that the catheter reaches to just below the Monro foramen. By suitable inclining of the head of the patient, the chain is then moved towards the fourth ventricle, whereafter the catheter is fed further along the chain. When the chain and the catheter have reached the point intended, the chain is withdrawn from the catheter and, for example, an injection may be made through the catheter. The introduction of the substance injected may be determined by X-ray television, for example the cerebro-spinal fluid must first be removed from the catheter.

Selective ventriculography is thus made possible in a simple manner. It is preferred that the catheter and the chain are advanced alternately, the latter being guided, thereby to facilitate the continued insertion. The chain must be able to move freely in the catheter with a minimum of friction, and the catheter must also be able to move freely in the cannula.

The invention may also be applied to advantage for the examination of the vascular system, in which the high degree of flexibility of the chain and the catheter used makes possible the penetration of said vascular system, with sharp curves and branches.

The invention makes possible the selective examination of particularly sensitive portions of the body. One important advantage is, because of the controllable insertion of the catheters, much less inserted contrast agent need be used than was previously the case, and said body portions can be studied without the disturbing influence of cavities of less diagnostic importance becoming filled with contrast medium. This provides less risk for the patient. Neither are the surroundings of the region which is of diagnostic interest shielded in a disturbing manner. Different contrast agents, for example liquid and gaseous, can be used simultaneously to fill different parts of the cavity being examined. This is particularly advantageous in the examination of the vessels of the brain and of the meninx when injecting contrast media or other substances.

The invention may also be applied to advantage for selective contrast examination or sampling in the system of body cavities comprising the trachea and airpipes.

Further, with the aid of the invention, blood vessel examinations can be carried out by inserting catheters into the vascular system, for examining by injecting contrast medium in desired localities, or by local application of foreign systems for therapeutical or diagnostic purposes.

It is also possible to introduce specially manufactured instruments for biopsy of structures in a cavity or of the walls thereof.

Expecially manufactured instruments may also be used for electrophysiological registration from solid substances adjacent cavities, or for stimulating such sites chemically or electrically, or for injecting a desired substance.

I claim as my invention:

1. Means for introducing a catheter into a selected portion of a patient, for conducting an object to such portion via the catheter, comprising:
    a. a cannula for insertion into an opening in the patient;
    b. a catheter slidably received in and externally guided by said cannula, said catheter having an inner flexible portion projecting inwardly beyond said cannula; and
    c. a freely flexible elongated member movable in response to gravity to such portion of a patient, and providing internal guidance for said inner flexible portion of said catheter, whereby said flexible member is moved by gravity through said cannula to the selected portion, then serves as a guide for insertion of said catheter to said selected portion, and is then removed from the catheter to enable the catheter to pass the object to said portion.

2. Means according to claim 1, wherein the insertion end of the flexible member is provided with a weight which is no thicker than the thickness of the flexible member.

3. Means according to claim 1, wherein the catheter is made of silicon rubber.

4. Means according to claim 1, wherein the flexible member is provided at its other end with a filament of rigid material for guiding the catheter upon passing the same over the flexible member.

5. Means according to claim 1, wherein the flexible member is made wholly or partially of a magnetic material, whereby the gravitational fall of the flexible member may be assisted by magnetic forces.

6. Means according to claim 1, wherein the catheter is provided with a radio-opaque point, at least at its insertion end.

7. Means according to claim 1, wherein the flexible member is in the form of a chain, such as of gold.

8. Means according to claim 7, wherein the chain has a weight at its insertion end, such in the shape of an olive.

9. Means according to claim 7, wherein the flexible chain is of a type known per se which can be locked in an adopted position by means actuatable from without.

10. A method for conducting an object to a selected portion of a patient, comprising:
    a. inserting a cannula into an opening in a patient;
    b. inserting a flexible elongated member through the cannula in response to gravity to such portion of the patient beyond the cannula;
    c. inserting a flexible catheter into the cannula in surrounding relation to the flexible elongated member by which elongated member the cannula is guided to such portion of the patient;
    d. withdrawing the flexible elongated member; and
    e. thereafter inserting the object into the catheter, to such portion of the patient.

* * * * *